United States Patent
Schönfeld et al.

(10) Patent No.: US 10,351,612 B2
(45) Date of Patent: Jul. 16, 2019

(54) INTERLEUKIN 15 AS SELECTABLE MARKER FOR GENE TRANSFER IN LYMPHOCYTES

(71) Applicant: CHEMOTHERAPEUTISCHES FORSCHUNGSINSTITUT GEORG-SPEYER-HAUS, Frankfurt am Main (DE)

(72) Inventors: Kurt Schönfeld, Langen (DE); Christiane Knopp, Langen (DE); Winfried Wels, Frankfurt am Main (DE)

(73) Assignee: CHEMOTHERAPEUTISCHES FORSCHUNGSINSTITUT GEORG-SPEYER-HAUS, Frankfurt am Main (DE)

( * ) Notice: Subject to any disclaimer, the term of this patent is extended or adjusted under 35 U.S.C. 154(b) by 212 days.

(21) Appl. No.: 15/269,731

(22) Filed: Sep. 19, 2016

(65) Prior Publication Data

US 2017/0044227 A1 Feb. 16, 2017

Related U.S. Application Data

(62) Division of application No. 13/821,474, filed as application No. PCT/EP2011/004491 on Sep. 6, 2011, now Pat. No. 9,487,800.

(30) Foreign Application Priority Data

Sep. 8, 2010 (EP) .................................... 10009346

(51) Int. Cl.
| | |
|---|---|
| A61K 35/12 | (2015.01) |
| C07K 14/54 | (2006.01) |
| C07K 14/725 | (2006.01) |
| C07K 14/705 | (2006.01) |
| C12N 15/85 | (2006.01) |
| C12N 15/86 | (2006.01) |
| A61K 35/17 | (2015.01) |
| C07K 16/18 | (2006.01) |

(52) U.S. Cl.
CPC .......... *C07K 14/5443* (2013.01); *A61K 35/17* (2013.01); *C07K 14/7051* (2013.01); *C07K 14/70517* (2013.01); *C07K 16/18* (2013.01); *C12N 15/85* (2013.01); *C12N 15/86* (2013.01); *A61K 2035/124* (2013.01); *C07K 2317/622* (2013.01); *C07K 2319/02* (2013.01); *C07K 2319/03* (2013.01); *C07K 2319/33* (2013.01); *C07K 2319/74* (2013.01); *C12N 2740/16043* (2013.01)

(58) Field of Classification Search
CPC combination set(s) only.
See application file for complete search history.

(56) References Cited

U.S. PATENT DOCUMENTS

2006/0263857 A1 11/2006 Lefrancois et al.

FOREIGN PATENT DOCUMENTS

WO WO 96/26274 A1 8/1996

OTHER PUBLICATIONS

Sadelain. Current Opinion in Immunology 21: 215-223, 2009.*
"Natural Killer (NK) cells" accessed at http://www.biology-pages.info/N/NK_Cells.html on Mar. 6, 2016, pp. 1-2.
Mortensen et al., Current Protocols in Molecular Biology, 9.5.1-9.5.19, 1997.
Kawahara et al., Nucleic Acid Research, 31(7), e32: 1-8, 2003.
Boissel et al., Leukemia Research, 33: 1255-1259, Jan. 2009.
Becknell, B. et al., "Interleukin-2, Inerleukin-15, and Their Roles in Human Natural Killer Cells", *Advances in Immunology*, 86: 209-239, 2005, Columbus, Ohio.
Budagian, V. et al., "IL-e15/IL-15 receptor biology: a guided tour through an expanding universe", *Cytokine Growth Factor Reviews*, 17(4): 259-280, Aug. 1, 2006, Elsevier, Netherlands.
Chong, S. et al., "Comparative ability of plasmid IL-12 and IL-15 to enhance cellular and humoral immune responses elicited by a SIV gag plasmid DNA vaccine and alter disease progression following SHIV(89.6P) challenge in rhesus macaques", Vaccine, 25(26): 4967-4982, Jun. 21, 2007, Elsevier, Netherlands.
Müller, T. et al., "Expression of a CD20-specific chimeric antigen receptor enhances cytotoxic activity of NK cells and overcomes NK-resistance of lymphoma and leukemia cells", *Cancer Immunology*, 57: 411-423, Aug. 24, 2007, Berlin, Germany.
Zhang, J. et al., "Characterization of Interleukin-15 gene-modified human natural killer cells: implications for adoptive cellular immunotherapy", *Haematologica* 89(3): 338-347, Mar. 1, 2004, Ferrata Storti Foundation, Italy.
Charrier, S. et al. (2010) Quantification of lentiviral vector copy numbers in individual hematopoietic colony-forming cells shows vector dose-dependent effects on the frequency and level of transduction. Gene Therapy, vol. 18, No. 5, 479-487.

(Continued)

*Primary Examiner* — Thaian N Ton
(74) *Attorney, Agent, or Firm* — Haug Partners LLP

(57) ABSTRACT

The present invention relates to the use of interleukin-15 (IL-15) as selectable marker for gene transfer, preferably of at least one gene of therapeutic interest, into a mammalian cell or cell line, in particular a human cell or cell line. The present invention furthermore relates to transgenic mammalian cells or cell lines expressing IL-15 as selectable marker and co-expressing at least one protein of interest encoded by at least one gene of interest, which is preferably a protein of therapeutic interest. The present invention is in particular suitable for chimeric antigen receptors (CARs) as the gene or protein of interest and their expression in lymphocytes. The transgenic mammalian cells and cell lines are furthermore suitable for use as a medicament, in particular in the treatment of cancer and in immunotherapy, such as adoptive, target-cell specific immunotherapy.

7 Claims, 6 Drawing Sheets

Specification includes a Sequence Listing.

(56) References Cited

OTHER PUBLICATIONS

Cohen, R.N. et al. (2009) Quantification of plasmid DNA copies in the nucleus after lipoplex and polyplex transfection. Journal of Controlled Release, vol. 135, No. 2, 166-174.

Quintarelli, C. et al. (2007) Co-expression of cytokine and suicide genes to enhance the activity and safety of tumor-specific cytotoxic T lymphocytes. Blood, vol. 110, No. 8, 2793-2802.

Wilkie, S. et al. (2010) Selective expansion of chimeric antigen receptor-targeted T-cells with potent effector function using interleukin-4. JBC, vol. 285, No. 33, 25538-25544.

Sahm, C. et al. (2012) Expression of IL-15 in NK cells results in rapid enrichment and selective cytotoxicity of gene-modified effectors that carry a tumor-specific antigen receptor. Cancer Immunology Immunotherapy, vol. 61, No. 9, 1451-1461.

Grabstein, Kenneth H. et al., Cloning of a T Cell Growth Factor that Interacts with the β Chain of the Interleukin-2 Receptor. Science, vol. 264, May 13, 1994, 965-968.

Uherek, C. et al., Retargeting of natural killer-cell cytolytic activity to ErbB2-expressing cancer cells results in efficient and selective tumor cell destruction. Blood, vol. 100, No. 4, Aug. 15, 2002, 1265-1273.

Office Action issued in corresponding European application No. 11 755 277.8.

\* cited by examiner

INTERLEUKIN 15 AS SELECTABLE MARKER FOR GENE TRANSFER IN LYMPHOCYTES

The present application is a Division of application Ser. No. 13/821,474, filed Mar. 7, 2013 (with a 371(c) date of May 28, 2013), which is a 371 of International Application No. PCT/EP2011/004491, filed Sep. 6, 2011, published on Oct. 11, 2012, under publication number WO 2012/136231, with a claim of priority under 35 USC 119 to Application No. 10 009 346.7, filed in Europe on Sep. 8, 2010, the entirety of which is incorporated herein by reference.

The present invention relates to the use of interleukin-15 (IL-15) as selectable marker for gene transfer, preferably of at least one gene of therapeutic interest, into a mammalian cell or cell line, in particular a human cell or cell line. The present invention furthermore relates to transgenic mammalian cells or cell lines expressing IL-15 as selectable marker and co-expressing at least one protein of interest encoded by at least one gene of interest, which is preferably a protein of therapeutic interest. The present invention is in particular suitable for chimeric antigen receptors (CARs) as the gene or protein of interest and their expression in lymphocytes. The transgenic mammalian cells and cell lines are furthermore suitable for use as a medicament, in particular in the treatment of cancer and in immunotherapy, such as adoptive, target-cell specific immunotherapy.

BACKGROUND OF THE INVENTION

T lymphocytes recognize specific antigens through interaction of the T cell receptor (TCR) with short peptides presented by major histocompatibility complex (MHC) class I or II molecules. For initial activation and clonal expansion, nave T cells are dependent on professional antigen-presenting cells (APCs) that provide additional co-stimulatory signals. TCR activation in the absence of co-stimulation can result in unresponsiveness and clonal anergy. To bypass immunization, different approaches for the derivation of cytotoxic effector cells with grafted recognition specificity have been developed. Chimeric antigen receptors (CARs) have been constructed that consist of binding domains derived from natural ligands or antibodies specific for cell-surface antigens, genetically fused to effector molecules such as the TCR alpha and beta chains, or components of the TCR-associated CD3 complex. Upon antigen binding, such chimeric antigen receptors link to endogenous signaling pathways in the effector cell and generate activating signals similar to those initiated by the TCR complex. Since the first reports on chimeric antigen receptors, this concept has steadily been refined and the molecular design of chimeric receptors has been optimized (for a review see Uherek et al., 2001). Aided by advances in recombinant antibody technology, chimeric antigen receptors targeted to a wide variety of antigens on the surface of cancer cells and of cells infected by human immunodeficiency virus (HIV) have been generated (for a review see Uherek et al., 2001).

The expression of CARs with specificity for tumor-associated or viral cell surface antigens in lymphocytes such as T cells or natural killer (NK) cells generates antigen-specific effector cells for the use in adoptive, target-cell specific immunotherapy. Such CARs are composed of a cell recognition domain such as a scFv antibody fragment for recognition of a tumor-cell surface antigen fused via a flexible linker region to an intracellular signaling domain such as CD3 zeta-chain. CAR expression retargets the cytotoxic activity of lymphocytes to tumor cells that are otherwise resistant to cytolysis by immune effector cells (Uherek et al., 2001; Uherek et al., 2002; Müller et al., 2008; Tavri et al., 2009). Thereby, gene transfer using viral vectors or physical transfection methods is of limited efficiency, resulting in only a fraction of the cells permanently incorporating and expressing the transferred gene construct. Hence, it is desirable to include a selectable marker gene in such vector constructs to allow selection and enrichment of gene-modified cells prior to therapeutic applications such as adoptive therapy.

Depending on the cell type used, the relatively low transduction efficiency of viral vectors employed for genetic modification of lymphocytes (in particular NK cells) with effector genes of therapeutic value (such as genes encoding CAR) limits the relative proportion of gene-modified cells in the transduced cell pool. In principle, inclusion of a selectable marker gene in the vector constructs would allow selection and enrichment of gene-modified cells prior to potential therapeutic applications in adoptive immunotherapy. However, available selection markers such as bacterial resistance genes and bacterial enzymes cannot be used due to their non-human origin and their potential immunogenicity. Furthermore, selection using such markers requires antibiotics or toxic reagents which must be added to the culture medium.

Therefore, the present invention aims to provide means and methods for the transfer of effector genes of therapeutic interest into mammalian (human) cells, in particular lymphocytes, utilizing a selectable marker gene of human origin which allows selective enrichment of gene-modified cells in standard culture medium without addition of toxic compounds.

Furthermore, the present invention aims to provide means and methods for medical application(s) of the mammalian (human) cells obtained thereby.

SUMMARY OF THE INVENTION

According to the present invention this object is solved by using interleukin-15 (IL-15) or functional equivalents thereof as selectable marker for/of gene transfer into a mammalian cell or cell line, wherein the mammalian cell or cell line is selected from effector cells of the immune system which require cytokines for growth and survival.

Thereby, upon gene transfer (of the IL-15 into said mammalian cell or cell line) the expression of the IL-15 as selectable marker results in survival or growth of the mammalian cell or cell line in the absence of said cytokines.

According to the present invention this object is furthermore solved by a transgenic mammalian cell or cell line expressing IL-15 as selectable marker for/of gene transfer and co-expressing at least one protein of interest (other than IL-15) encoded by at least one gene of interest (other than IL-15), wherein the mammalian cell or cell line is selected from effector cells of the immune system which require cytokines for growth and survival and wherein the expression of the IL-15 as selectable marker results in survival or growth of the mammalian cell or cell line in the absence of said cytokines.

According to the present invention this object is furthermore solved by the transgenic mammalian cell or cell line of the invention for use as a medicament.

According to the present invention this object is furthermore solved by the transgenic mammalian cell or cell line of the invention for use in the treatment of cancer or in immunotherapy.

DESCRIPTION OF THE PREFERRED EMBODIMENTS OF THE INVENTION

Before the present invention is described in more detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art. For the purpose of the present invention, all references cited herein are incorporated by reference in their entireties.

Interleukin-15 as Selectable Marker for Gene Transfer

As described above, the present invention provides the use of interleukin-15 (IL-15) or functional equivalents thereof as selectable marker for gene transfer into a mammalian cell or cell line.

Thereby, the expression of said IL-15 as selectable marker results in survival or growth of the mammalian cell or cell line.

IL-15

Interleukin 15 (IL-15) belongs to the IL-15/IL-21 family of cytokines. IL-15 has biological activities similar to IL-2, and has been shown to stimulate the growth of natural killer cells, activated peripheral blood T lymphocytes, tumor infiltrating lymphocytes (TILs), and B cells. In addition, IL-15 has also been shown to be a chemoattractant for human blood T lymphocytes, and to be able to induce lymphokine-activated killer (LAK) activity in NK cells and to induce the generation of cytolytic effector cells. The IL-15 cDNA encodes a 162 amino acid (aa) residue precursor protein containing a 48 aa residue leader that is cleaved to generate the 114 aa residue mature IL-15. In humans, interleukin 15 is encoded by the IL15 gene. Like IL-2, IL-15 binds to and signals through the IL-2/IL-15 beta chain (CD122) and the common gamma chain (gamma-C, CD132). Other cytokines which signal through receptor complexes that contain the common gamma chain but employ a receptor beta chain different from that of the IL-15 and IL-2 receptor complexes, include IL-4, IL-7, IL-9, and IL-21.

According to the invention, the IL-15 used is human IL-15:

The amino acid sequence of *homo sapiens* interleukin 15 (IL-15) preproprotein (Genbank Accession No. NP_000576.1):

```
Amino acid sequence
                                         [SEQ ID NO. 1]
  MRISKPHLRS ISIQCYLCLL LNSHFLTEAG IHVFILGCFS

AGLPKTEANW VNVISDLKKI EDLIQSMHID ATLYTESDVH

PSCKVTAMKC FLLELQVISL ESGDASIHDT VENLIILANN

SLSSNGNVTE SGCKECEELE EKNIKEFLQS FVHIVQMFIN TS
```

The protein encoding nucleotide sequence including the translation stop codon of *homo sapiens* interleukin 15 (IL-15) cDNA, representing nucleotides 370-858 of interleukin 15 transcript variant 3 (Genbank Accession No. NM_000585.3):

```
Nucleotide sequence
                                         [SEQ ID NO. 2]
ATGAGAATTTCGAAACCACATTTGAGAAGTATTTCCATCCAGTGCTACTT

GTGTTTACTTCTAAACAGTCATTTTCTAACTGAAGCTGGCATTCATGTCT

TCATTTTGGGCTGTTTCAGTGCAGGGCTTCCTAAAACAGAAGCCAACTGG

GTGAATGTAATAAGTGATTTGAAAAAAATTGAAGATCTTATTCAATCTAT

GCATATTGATGCTACTTTATATACGGAAAGTGATGTTCACCCCAGTTGCA

AAGTAACAGCAATGAAGTGCTTTCTCTTGGAGTTACAA.GTTATTTCACT

TGAGTCCGGAGATGCAAGTATTCATGATACAGTAGAAAATCTGATCATCC

TAGCAAACAACAGTTTGTCTTCTAATGGGAATGTAACAGAATCTGGATGC

AAAGAATGTGAGGAACTGGAGGAAAAAAATATTAAAGAATTTTTGCAGAG

TTTTGTACATATTGTCCAAATGTTCATCAACACTTCTTGA
```

In an embodiment, the IL-15 nucleic acid sequence can be codon-optimized for expression in mammalian cells, preferably for expression in human cells.

According to the invention, the IL-15 used is human IL-15 with the amino acid sequence of SEQ ID NO. 1 or an amino acid sequence that has at least 95% sequence identity or 99% sequence identity to the amino acid sequence of SEQ ID NO. 1;

or the IL-15 used is human IL-15 encoded by the nucleotide sequence of SEQ ID NO. 2 or a nucleotide sequence with at least 95% sequence identity or 99% sequence identity to the nucleotide sequence of SEQ ID NO. 2.

Codon-optimization refers to the exchange in a sequence of interest of codons that are generally rare in highly expressed genes of a given species by codons that are generally frequent in highly expressed genes of such species, such codons encoding the same amino acids as the codons that are being exchanged.

The skilled artisan will be able to design and utilize suitable codon optimizations of the above sequences.

Within the scope of this invention are also the nucleotide sequences obtained due to the degeneration of the genetic code of the nucleotide sequences disclosed herein.

The IL-15 is preferably comprised in an expression or gene construct, which is transferred into the mammalian cell or cell line.

An "expression or gene construct" (wherein both terms are used interchangeably throughout this specification) refers to a nucleic acid construct, usually an expression vector or plasmid, that is used to introduce a specific gene sequence into a target cell. Once the expression or gene construct is inside the cell, the protein that is encoded by the gene is produced by the cellular transcription and translation machinery. The expression or gene construct is designed to contain respective regulatory sequences that act as enhancer and promoter regions and lead to efficient transcription of the gene carried on the construct, including promoter and terminator sequences). The goal of a well-designed expression or gene construct is the production of large amounts of stable mRNA, and therefore proteins.

In an embodiment of an expression or gene construct according to this invention, a nucleotide sequence encoding (human) IL-15, i.e. a coding sequence of (human) IL-15, and a gene of interest are separated by a regulatory element, preferably an internal ribosome entry site (IRES), enabling their simultaneous expression under the control of a single promoter.

The expression or gene construct comprising the IL-15 is preferably a (DNA) plasmid or a viral vector, such as a lentiviral vector, a gamma-retroviral vector or an adeno-associated virus vector.

The nucleic acids of this invention comprise DNA (such as dsDNA, ssDNA, cDNA), RNA (such as dsRNA, ssRNA, mRNA), combinations thereof or derivatives (such as PNA) thereof.

The expression or gene construct comprises a nucleotide sequence encoding (human) IL-15, i.e. a coding sequence of (human) IL-15.

The coding sequence of (human) IL-15 is preferably a cDNA of (human) IL-15.

The coding sequence of IL-15 is preferably
the nucleotide sequence encoding human IL-15 with the amino acid sequence of SEQ ID NO. 1 or functional equivalents thereof,
the nucleotide sequence comprising or having the nucleotide sequence of human IL-15 transcript variant 3 of SEQ ID NO. 2 or functional equivalents thereof,
or complementary sequences thereof
or codon-optimized sequences thereof,
or nucleotide sequences encoding amino acid sequences with at least 95% sequence identity or 99% sequence identity to the amino acid sequence of SEQ ID NO. 1,
or nucleotide sequences with at least 95% sequence identity or 99% sequence identity to the nucleotide sequence of SEQ ID NO. 2.

The term "functional equivalent" defines a protein or nucleotide sequence, having a different amino acid or base sequence, compared to the sequences disclosed herein, but exhibiting the same function in vitro and in vivo. An example of a functional equivalent is a modified or synthetic gene, encoding the expression of a protein identical or highly homologous to that encoded by the wildtype gene.

A "functional equivalent" of (human) IL-15 refers to a protein that has an amino acid sequence or nucleotide sequence encoding therefore with less than 100% sequence identity to SEQ ID NO. 1 or 2, respectively, but functions as IL-15 inside a cell (the host cell), which means that said protein binds to the IL-15 receptor complex and initiates signalling through beta and gamma chains of such receptor complex in a manner similar to IL-15. Such binding to the IL-15 receptor complex can be measured using suitable techniques such as flow cytometry which are known to the skilled artisan.

Preferably, the IL-15 is directly utilized by the mammalian cell or cell line expressing it and is not secreted to the culture supernatant in amounts supporting the growth and survival of bystander cells which do not express IL-15 themselves.

Selectable Marker for Gene Transfer

A marker gene is a suitable means in molecular biology for determining whether the transfer of specific nucleic acid(s) (such as DNA, herein gene of interest or effector gene) into a host cell has been successful. There are two types of marker genes: selectable markers and markers for screening.

A "selectable marker" or "selection marker" will either protect the host cell from a selective agent that would normally kill it or prevent its growth or is required for the host cells growth and survival. It is a gene introduced into the host cell that confers a trait suitable for artificial selection.

In most applications, only one in several hundred cells will take up the specific nucleic acid(s) (such as DNA encoding a gene/protein of interest). Rather than checking every single cell, a selective agent is used to kill all cells that do not contain the foreign nucleic acid(s) or only allows cells containing the foreign nucleic acid(s) to grow, thus, leaving only the desired ones. As discussed above, selectable markers are often antibiotic resistance genes or bacterial enzymes.

Thus, a "selectable marker" is a gene whose expression allows one to identify and selectively enrich cells that have been transformed, transfected or transduced with a nucleic acid construct containing the marker gene.

The term "gene transfer" refers to the introduction of a nucleic acid (construct) (expression or gene construct) of interest into the mammalian cell or cell line by any way, such as transformation, transfection, microinjection, particle-mediated transfer, transduction with a viral vector. These techniques are known to the skilled artisan.

According to the invention, IL-15 is used as selectable marker for ex vivo or in vitro gene transfer.

According to the invention, IL-15 is used as selectable marker for the gene transfer of another nucleic acid or gene, which is transferred into the host cell at the same time (i.e. together with the IL-15).

Said other nucleic acid or gene is a "gene of interest" or "effector gene" (wherein these terms are used interchangeably throughout this specification) which encodes a "protein of interest" or "effector protein" (wherein these terms are used interchangeably throughout this specification).

Preferably, the gene transfer into the mammalian cell or cell line, for which IL-15 is used as the selectable marker, is the transfer of IL-15 together with at least one gene of interest (other than IL-15) encoding a protein of interest (other than IL-15) into the mammalian cell or cell line.

Thereby, the nucleic acid/coding sequence of IL-15 and the at least one gene of interest are transferred into the cell using one/the same expression or gene construct or using different expression or gene constructs.

In other embodiments of the invention, more than one gene of interest each encoding a protein of interest is/are transferred into the mammalian cell or cell line, such as two, three, four or more genes of interest.

The at least one gene of interest preferably encodes a protein of therapeutic interest, preferably a chimeric antigenic receptor (CAR).

Host Cells

Preferably, the mammalian cell or cell line is a human cell or cell line.

The mammalian cell or cell line, in particular the human cell or cell line, requires cytokines for growth and survival when it is not modified, i.e. not expressing IL-15. Said cytokines are preferably one or more cytokine that bind to a receptor complex that contains the common gamma chain of the IL-2 receptor and include but are not limited to the cytokines IL-2, IL-4, IL-7, IL-9, IL-15 and IL-21, more preferably IL-2.

In particular, the mammalian cell or cell line, in particular the human cell or cell line, is in non-modified state preferably dependent on said cytokine(s) for its growth and survival and is unable to produce any significant amounts of IL-15, but in modified state it produces IL-15 in an amount sufficient to sustain growth and survival without the need of said cytokine(s). In in vitro culture, the mammalian cell or cell line, in particular the human cell or cell line, requires for growth and survival in non-modified state that above cytokines are added exogenously.

According to the invention, the mammalian cell or cell line is selected from effector cells of the immune system, such as lymphocytes including but not limited to cytotoxic lymphocytes, T cells, cytotoxic T cells, T helper cells, Th17 T cells, natural killer (NK) cells, natural killer T (NKT) cells, mast cells, dendritic cells, killer dendritic cells, B cells.

According to the invention, the mammalian cell or cell line is selected from effector cells of the immune system which require cytokines (preferably one or more cytokine that bind to a receptor complex that contains the common gamma chain of the IL-2 receptor and include but are not limited to the cytokines IL-2, IL-4, IL-7, IL-9, IL-15 and IL-21, more preferably IL-2) for growth and survival.

More preferably, the human cell or cell line is selected from natural killer (NK) cells and T cells (such as cytotoxic T lymphocytes (CTLs)).

Due to the endogenous expression of IL-15 as selectable marker gene, the mammalian cells of the invention do not require, in in vitro culture, any exogenously added cytokines (preferably one or more cytokine that bind to a receptor complex that contains the common gamma chain of the IL-2 receptor and include but are not limited to the cytokines IL-2, IL-4, IL-7, IL-9, IL-15 and IL-21, more preferably IL-2) for growth and survival, which allows the selection of these cells by withdrawal of the exogenous cytokines, which e.g. has advantages for the use of these cells in in vivo applications.

Thus, the present invention provides the use of interleukin-15 (IL-15) as selectable marker for ex vivo or in vitro gene transfer into a mammalian cell or cell line, wherein the mammalian cell or cell line is selected from effector cells of the immune system which require cytokines for growth and survival, wherein said cytokines include but are not limited to IL-2, IL-4, IL-7, IL-9, IL-15 and IL-21, wherein upon gene transfer of the IL-15 into said mammalian cell or cell line the expression of the IL-15 as selectable marker results in survival or growth of the mammalian cell or cell line in the absence of said cytokines, wherein the IL-15 has the amino acid sequence of SEQ ID NO. 1 or an amino acid sequence that has at least 95% sequence identity to SEQ ID NO. 1, or is encoded by the nucleotide sequence of SEQ ID NO. 2 or a nucleotide sequence with at least 95% sequence identity to SEQ ID NO. 2.

Expression of chimeric antigen receptors (CAR) with defined target-cell specificity in lymphocytes results in genetically modified variants of the lymphocytes that selectively target and eliminate defined target cells including but not limited to malignant cells carrying a respective tumor-associated surface antigen or virus infected cells carrying a virus-specific surface antigen (Uherek et al., 2001). Thereby gamma-retroviral or lentiviral vectors are commonly employed for gene transfer into cytotoxic lymphocytes, but depending on the particular cell type used this can result in only a small proportion of cells being transduced successfully. Object matter of the invention are methods and means such as gene constructs for expression in lymphocytes that carry cDNA of human interleukin-15 (IL-15) as a selectable marker gene in addition to another gene of interest such as a CAR or another(other) gene(s) of interest with therapeutic value.

As discussed above, depending on the cell type used, the relatively low transduction efficiency of viral vectors employed for genetic modification of lymphocytes, in particular NK cells, with effector genes of therapeutic value such as genes encoding CAR limits the relative proportion of gene-modified cells in the transduced cell pool. In principle, inclusion of a selectable marker gene in the vector constructs would allow selection and enrichment of gene-modified cells prior to potential therapeutic applications in adoptive immunotherapy. However, available selection markers such as bacterial resistance genes and bacterial enzymes cannot be used due to their non-human origin and their potential immunogenicity. Furthermore, selection using such markers requires antibiotics or toxic reagents which must be added to the culture medium. Therefore the aim of the technical solution described herein was the generation of methods and means such as vectors for gene transfer into lymphocytes that contain a selectable marker gene of human origin which allows selective enrichment of gene-modified cells in standard culture medium without addition of toxic compounds. Cytotoxic lymphocytes such as NK cells or CTL require (exogenous) cytokines (e.g. IL-2) for growth and survival, which can at the same time be substituted with the related cytokine IL-15 used as the selectable marker.

Object matter of the invention are gene constructs for expression in lymphocytes that carry cDNA of human interleukin-15 (IL-15) as a selectable marker gene in addition to another gene of interest such as a CAR or another effector gene of therapeutic value. After gene transfer into cytokine-dependent lymphocytes like NK cells or T lymphocytes, only cells that have successfully incorporated the transferred construct are able to grow in the absence of exogenously added cytokines and can such be selected for simply by withdrawal of exogenous cytokines. At the same time this autocrine production of IL-15 provides the gene-modified lymphocytes with a growth and survival signal indispensable for their continued functional activity.

The inventors have now demonstrated the suitability or use of IL-15 as selectable marker gene. Our technical solution is not based on IL-2 but on the use of IL-15. Thereby, using IL-15 circumvents potential side effects of IL-2 in vivo, since IL-15 does not support the suppressing activity of regulatory T cells (Wuest et al., 2008). In contrast to Zhang et al., who previously described expression of IL-15 in NK cells (Zhang et al., 2004), our technical solution allows only growth of NK cells transduced with constructs (vectors) encoding IL-15 in the complete absence of exogenous cytokines, which is a requirement for the use of IL-15 as a selection marker. NK cells expressing such constructs according to the invention do not secrete measurable amounts of IL-15 into the culture supernatant but utilize all IL-15 produced endogenously. Hence, IL-15 expressing NK cells do not support the growth or survival of IL-15 negative bystander cells making IL-15 suitable as selectable marker gene (as has been demonstrated in e.g. FIG. 6)

According to the invention, the expression of the IL-15 does not result in the secretion of IL-15 into the culture supernatant in amounts sufficient to support survival and growth of cells that are not transformed or transduced with the IL-15 and/or are not expressing the IL-15 themselves.

Embodiment wherein the Protein of Therapeutic Interest is a CAR

In one embodiment of the invention the protein of therapeutic interest is a chimeric antigen receptor (CAR).

A CAR comprises
(i) a signal peptide;
(ii) a target specific recognition domain, binding an antigen, receptor, peptide ligand or protein ligand of the target, wherein the target is a cell or a virus;
(iii) a linker region, connecting domain (ii) and domain (iv); and
(iv) an effector domain comprising a transmembrane region and one or more intracellular signaling domains.

A "chimeric antigen receptor" is a cell surface receptor protein and, thus, comprises an extracellular portion (domains (i) and (ii) and (iii)), a transmembrane portion (contributed by/comprised in domain (iv)) and a cytoplasmic portion (contributed by/comprised in domain (iv)), and can thus be inserted into the plasma membrane of the host cell. The functionality of a CAR within a host cell is detectable in an assay suitable for demonstrating the signaling potential of said protein upon binding of a particular ligand. Such assays are available to the skilled artisan. Upon binding to the target, CARs link to endogenous signaling pathways in a cell (an effector cell) and generate certain activating signals (depending on the effector domain).

The target specific recognition domain (ii) binds an antigen, receptor, peptide ligand or protein ligand of the target.

The target specific recognition domain (ii) preferably comprises an antigen binding domain derived from an antibody against an antigen of the target, or a peptide binding an antigen of the target, or a peptide or protein binding an antibody that binds an antigen of the target, or a peptide or protein ligand (including but not limited to a growth factor, a cytokine or a hormone) binding a receptor on the target, or a domain derived from a receptor (including but not limited to a growth factor receptor, a cytokine receptor or a hormone receptor) binding a peptide or protein ligand on the target.

Preferably, the target is a cell or a virus.

The target specific recognition domain serves for the targeting of the CAR or a respective cell expressing/carrying the CAR on its surface to a specific target. Binding of the target specific recognition domain of the CAR to its cognate target on the surface of target cells/viruses furthermore transmits a signal into the CAR-expressing immune effector cells via the intracellular signaling domain(s) of the CAR which activates the endogenous cytotoxic activity of such immune effector cells.

Where domain (ii) of the CAR binds an antigen of the target, examples of the antigen are a tumor-associated surface antigen (such as ErbB2 (HER2/neu), carcinoembryonic antigen (CEA), epithelial cell adhesion molecule (EpCAM), epidermal growth factor receptor (EGFR), EGFR variant III (EGFRvIII), CD19, CD20, CD30, CD40, disialoganglioside GD2, a major histocompatibility complex (MHC) molecule presenting a tumor-specific peptide epitope);

a lineage-specific or tissue-specific surface antigen (such as CD3, CD4, CD8, CD24, CD25, CD33, CD34, CD133, CD138, CTLA-4, B7-1 (CD80), B7-2 (CD86), endoglin, a major histocompatibility complex (MHC) molecule) or a virus-specific surface antigen (such as an HIV-specific antigen (e.g. HIV gp120), an EBV-specific antigen, a CMV-specific antigen, a HPV-specific antigen, a HBV-specific antigen, a HCV-specific antigen, a Lassa Virus-specific antigen, an Influenza Virus-specific antigen).

Where domain (ii) of the CAR comprises an antigen binding domain, the antigen binding domain is preferably derived from an antibody or an antibody fragment, such as a single chain Fv (scFv) fragment, a Fab fragment, a diabody, a variable domain of the antibody heavy chain or antibody light chain.

More preferably, the domain (ii) of the CAR binds an antigen of the target and the antigen is a tumor-associated surface antigen, such as EpCAM or ErbB2.

The linker region (iii) of the CAR connects the target specific recognition domain (ii) and the effector domain (iv). The linker region serves as a flexible spacer between the target specific recognition domain (ii) and the effector domain (iv). It ensures the necessary accessibility and flexibility of the target specific recognition domain (ii). The linker region is understood to be essential for the functionality of the CARs.

CARs typically contain a linker region derived from the alpha-chain of the human CD8 molecule which provides a flexible connection between cell-targeting and signaling/effector domains (Uherek et al., 2002; Müller et al., 2008).

In one embodiment, the linker region (iii) of the CAR comprises a hinge region derived from the human CD8 alpha-chain, wherein said human CD8 alpha-chain hinge region has preferably the amino acid sequence of SEQ ID NO. 3, or an amino acid sequence that has at least 80% sequence identity to the amino acid sequence of SEQ ID NO. 3, preferably at least 90% sequence identity, more preferably at least 95% sequence identity or 99% sequence identity to the amino acid sequence of SEQ ID NO. 3, or an amino acid sequence that differs in one, two, three, four or more, up to twelve, amino acid residues from the amino acid sequence of SEQ ID NO. 3 (i.e. differs in one, two, three, four, five, six, seven, eight, nine, ten, eleven or twelve), wherein "differ" refers to replacement/substitution, addition or deletion, such as conservative substitution(s) of amino acid residues.

SEQ ID NO. 3:
ALSNSIMYFSHFVPVFLPAKPTTTPAPRPPTPAPTIASQPLSLRPEACRP

AAGGAVHTRGLD

The effector domain (iv) of the CAR comprises a transmembrane region and one or more intracellular signaling domains. The effector domain serves the coupling of the target/antigen recognition to the intracellular signaling machinery. Binding of the target specific recognition domain (ii) of the CAR to its cognate target on the surface of target cells/viruses furthermore transmits a signal into the CAR-expressing immune effector cells via the intracellular signaling domain(s) of the CAR (which are part of the effector domain) which activates the endogenous cytotoxic activity of such immune effector cells.

In an embodiment, the effector domain (iv) comprises or consists of (is) the zeta-chain of the human CD3 complex of the T-cell receptor or a fragment thereof or a functional equivalent thereof or a fusion with a further protein (or fragment thereof), such as a fragment of the human costimulatory CD28 receptor.

In an embodiment, the zeta-chain of the human CD3 complex of the T-cell receptor has the amino acid sequence of SEQ ID NO. 4.

A "functional equivalent" has less sequence identity (such as at least 80% sequence identity, preferably at least 90% sequence identity, more preferably at least 95% sequence identity or 99% sequence identity) but is a functional zeta-chain of the CD3 complex of the T-cell receptor. According to the invention, the zeta chain is of human origin. Within the TCR the CD3 zeta chain exists as a disulfide homodimer. A "functional CD3 zeta chain" or "a functional zeta-chain of the CD3 complex of the T-cell receptor" is a protein which upon expression in T cell hybridomas deficient in endogenous zeta expression is capable of restoring in said hybridomas a functionally active TCR.

Generally, a person skilled in the art is aware of the fact that some amino acid exchanges in the amino acid sequence of a protein or peptide do not have any influence on the (secondary or tertiary) structure, function and activity of the protein or peptide (at all). Amino acid sequences with such "neutral" amino acid exchanges as compared to the amino acid sequences disclosed herein fall within the scope of the present invention.

Transgenic Cells Expressing IL-15 and a Gene of Interest

As described above, the present invention provides transgenic mammalian cells or cell lines expressing IL-15 as selectable marker and co-expressing at least one protein of interest (other than IL-15) encoded by at least one gene of interest (other than IL-15).

Preferably, the transgenic mammalian cell or cell line is a human cell or cell line.

The mammalian cell or cell line, in particular the human cell or cell line, requires cytokines for growth and survival when it is not modified, i.e. not expressing IL-15. Said cytokines are preferably one or more cytokine that bind to a receptor complex that contains the common gamma chain of the IL-2 receptor and include but are not limited to the cytokines IL-2, IL-4, IL-7, IL-9, IL-15 and IL-21, more preferably IL-2.

In particular, the mammalian cell or cell line, in particular the human cell or cell line, is in non-modified state preferably dependent on said cytokine(s) for its growth and survival and is unable to produce any significant amounts of IL-15, but in modified state it produces IL-15 in an amount sufficient to sustain growth and survival without the need of said cytokine(s). In in vitro culture, the mammalian cell or cell line, in particular the human cell or cell line, requires for growth and survival in non-modified state that above cytokines are added exogenously.

According to the invention, the transgenic mammalian cell or cell line is selected from effector cells of the immune system, such as lymphocytes including but not limited to cytotoxic lymphocytes, T cells, cytotoxic T cells, T helper cells, Th17 T cells, natural killer (NK) cells, natural killer T (NKT) cells, mast cells, dendritic cells, killer dendritic cells, B cells.

According to the invention, the transgenic mammalian cell or cell line is selected from effector cells of the immune system which require cytokines (preferably one or more cytokine that bind to a receptor complex that contains the common gamma chain of the IL-2 receptor and include but are not limited to the cytokines IL-2, IL-4, IL-7, IL-9, IL-15 and IL-21, more preferably IL-2) for growth and survival.

Preferably, the human cell or cell line is selected from natural killer (NK) cells and T cells (such as cytotoxic T lymphocytes (CTLs)), Due to the endogenous expression of IL-15 as selectable marker gene, the mammalian cells of the invention do not require, in in vitro culture, any exogenously added cytokines (preferably one or more cytokine that bind to a receptor complex that contains the common gamma chain of the IL-2 receptor and include but are not limited to the cytokines IL-2, IL-4, IL-7, IL-9, IL-15 and IL-21, more preferably IL-2) for growth and survival, which allows the selection of these cells by withdrawal of the exogenous cytokines, which e.g. has advantages for the use of these cells in in vivo applications.

The present invention provides a transgenic mammalian cell or cell line expressing IL-15, as defined herein, as selectable marker for gene transfer and co-expressing at least one protein of interest encoded by at least one gene of interest, wherein the mammalian cell or cell line is selected from effector cells of the immune system which require cytokines for growth and survival, wherein said cytokines include but are not limited to IL-2, IL-4, IL-7, IL-9, IL-15 and IL-21, wherein the protein of interest is a protein other than IL-15 and the gene of interest is a gene other than IL-15, and wherein (upon gene transfer of the IL-15 and the gene/protein of interest into said mammalian cell or cell line) the expression of the IL-15 as selectable marker results in survival or growth of the mammalian cell or cell line in the absence of said cytokines.

Preferably (and as has been discussed herein), the expression of the IL-15 does not result in the secretion of IL-15 into the culture supernatant in amounts sufficient to support survival and growth of cells that are not transformed or transduced with the IL-15 and/or are not expressing the IL-15 themselves.

The IL-15 (gene) and the at least one gene of interest can be transferred into the transgenic cell of the invention using:

(a) one expression or gene construct which comprises both a nucleotide sequence encoding (human) IL-15, i.e. a coding sequence of (human) IL-15, and the gene of interest, or (b) different expression or gene constructs (at least two) wherein one construct comprises a nucleotide sequence encoding (human) IL-15, i.e. a coding sequence of (human) IL-15, and the other construct(s) comprise(s) the gene(s) of interest.

An "expression or gene construct" (wherein both terms are used interchangeably throughout this specification) refers to a nucleic acid construct, usually an expression vector or plasmid, that is used to introduce a specific gene sequence into a target cell. Once the expression or gene construct is inside the cell, the protein that is encoded by the gene is produced by the cellular transcription and translation machinery. The expression or gene construct is designed to contain respective regulatory sequences that act as enhancer and promoter regions and lead to efficient transcription of the gene carried on the construct, including promoter and terminator sequences). The goal of a well-designed expression or gene construct is the production of large amounts of stable mRNA, and therefore proteins.

In an embodiment of the invention utilizing one expression construct (a), the coding sequence of (human) IL-15 and the gene of interest are separated by a regulatory element, preferably an internal ribosome entry site (IRES), enabling their simultaneous expression under the control of a single promoter.

The expression or gene construct comprising the IL-15 (gene) and/or the at least one gene of interest is preferably a (DNA) plasmid or a viral vector, such as a lentiviral vector, a gamma-retroviral vector or an adeno-associated virus vector.

The nucleic acids of this invention comprise DNA (such as dsDNA, ssDNA, cDNA), RNA (such as dsRNA, ssRNA, mRNA), combinations thereof or derivatives (such as PNA) thereof.

The expression or gene construct comprises a nucleotide sequence encoding (human) IL-15, i.e. a coding sequence of (human) IL-15, as defined herein above.

Suitable expression or gene constructs and plasmids are known to the skilled artisan, such as (DNA) plasmids or viral vectors (e.g. lentiviral vector, a gamma-retroviral vector or an adeno-associated virus vector).

In other embodiments of the invention, more than one gene of interest each encoding an protein of interest is transferred into the mammalian cell or cell line, such as two, three, four or more genes of interest.

Preferably, the at least one gene of interest encodes a protein of therapeutic interest.

In an embodiment, the protein of therapeutic interest is a chimeric antigenic receptor (CAR), wherein the CAR is as defined herein above.

The present invention also encompasses a method of producing transgenic (gene-modified) mammalian cells or cell lines expressing IL-15 as selectable marker and co-expressing at least one protein of interest encoded by at least one gene of interest, wherein the method comprises:
- selection and construction of expression or gene construct(s) comprising either (a—one construct) both a nucleotide sequence encoding (human) IL-15, i.e. a coding sequence of (human) IL-15, and the gene of interest, or (b—different constructs) comprising a nucleotide sequence encoding (human) IL-15, i.e. a coding sequence of (human) IL-15, or the gene(s) of interest;
- genetic modification of the cells by transfer of the expression or gene construct(s) into the cell;
- selection of the transgenic (gene-modified) cells.

Medical Uses of the Transgenic Cells

As described above, the present invention provides the transgenic mammalian cells or cell lines of the invention (which express IL-15 as selectable marker and co-express at least one protein of interest encoded by at least one gene of interest) for use as a medicament.

As described above, the present invention provides the transgenic mammalian cells or cell lines of the invention (which express IL-15 as selectable marker and co-express at least one protein of interest encoded by at least one gene of interest) for use in the treatment of cancer or in immunotherapy, preferably in adoptive, target-cell specific immunotherapy.

"Adoptive, target-cell specific immunotherapy" refers to a form of therapy in which immune cells are transferred to tumor-bearing hosts. The immune cells have antitumor reactivity and can mediate direct or indirect antitumor effects.

"Adoptive, target-cell specific immunotherapy" or "adoptive cell therapy (ACT)" is a treatment that uses immune effector cells, such as lymphocytes with anti-tumour activity, expanded in vitro and infused into the patient with cancer. ACT using autologous tumour-infiltrating lymphocytes has emerged as the most effective treatment for patients with metastatic melanoma and can mediate objective cancer regression in approximately 50% of patients. The use of donor lymphocytes for ACT is an effective treatment for immunosuppressed patients who develop post-transplant lymphomas (reviewed in Rosenberg et al., 2008). However, the ability to genetically engineer human lymphocytes and use them to mediate cancer regression in patients, which has recently been demonstrated (see Morgan et al, 2006), has opened possibilities for the extension of ACT immunotherapy to patients with a wide variety of cancer types and is a promising new approach to cancer treatment. Thus, lymphocytes genetically engineered with chimeric antigen receptors (CAR), such as provided by this invention, are very suitable for ACT and open more possibilities in the treatment of cancer. Especially, since studies have clearly demonstrated that the administration of highly avid anti-tumour T cells directed against a suitable target can mediate the regression of large, vascularized, metastatic cancers in humans and provide guiding principles as well as encouragement for the further development of immunotherapy for the treatment of patients with cancer.

The mammalian cells and cell lines of the invention, in particular the human immune effector cells, are very suitable for medical applications, in particular for ACT, because:
- they carry a selectable marker of human origin (thus not eliciting an immune response);
- they require no exogenous cytokines for growth and survival;
- they show highly functional CAR-mediated cytotoxicity in absence of exogenous cytokines (in the embodiment with a CAR as a protein/gene of interest);
- they do not support the growth of IL-15 negative bystander cells, because the effect of the IL-15 is limited to the cell producing it;
- they utilize the IL-15 produced endogenously and do not secrete measurable amounts of IL-15 into the culture supernatant;
- they are designed for the coexpression of at least one gene of therapeutic interest.

Treatment Methods

Furthermore, the present invention provides methods for the treatment of diseases, in particular cancer, and methods of immunotherapy, preferably including adoptive, target-cell specific immunotherapy.

The method for the treatment of diseases, in particular cancer, according to the present invention comprises
administering to a subject in a therapeutically effective amount
(a) a transgenic mammalian cell or cell line as obtained and defined herein above; and
(b) optionally, respective excipient(s).

The method of immunotherapy, preferably including or utilizing adoptive, target-cell specific immunotherapy, according to the present invention comprises
administering to a subject in a therapeutically effective amount
(a) a transgenic mammalian cell or cell line as obtained and defined herein above; and
(b) optionally, respective excipient(s).

A "therapeutically effective amount" of a transgenic mammalian cell or cell line of this invention refers to the amount that is sufficient to treat the respective disease or achieve the respective outcome of the adoptive, target-cell specific immunotherapy.

The following examples and drawings illustrate the present invention without, however, limiting the same thereto.

(A) Analysis of CAR surface expression. Expression of CAR on the surface of NK/CAR IL-15 cells was investigated by FACS analysis using an antibody detecting a sequence tag included in the EpCAM-specific CAR (dark gray). NK cells transduced with IRES-IL-15 vector served as control (light gray).

(B)-(D) NK cells co-expressing CAR and IL-15 (NK/CAR IL-15) or NK cells only expressing IL-15 (NK/IRES-IL-15) were co-cultured in the absence of exogenous cytokines at different effector to target (E:T) ratios with NK-sensitive K562 erythroleukemic control cells (B), EpCAM-expressing MDA-MB468 breast carcinoma cells (C), or EpCAM-negative MDA-MB435 melanoma cells (D). As shown in (C), NK cells expressing IL-15 and the EpCAM-specific CAR showed EpCAM-specific and highly effective cell killing (open bars) when compared to NK cells expressing IL-15 but no CAR (filled bars).

Figure 5:
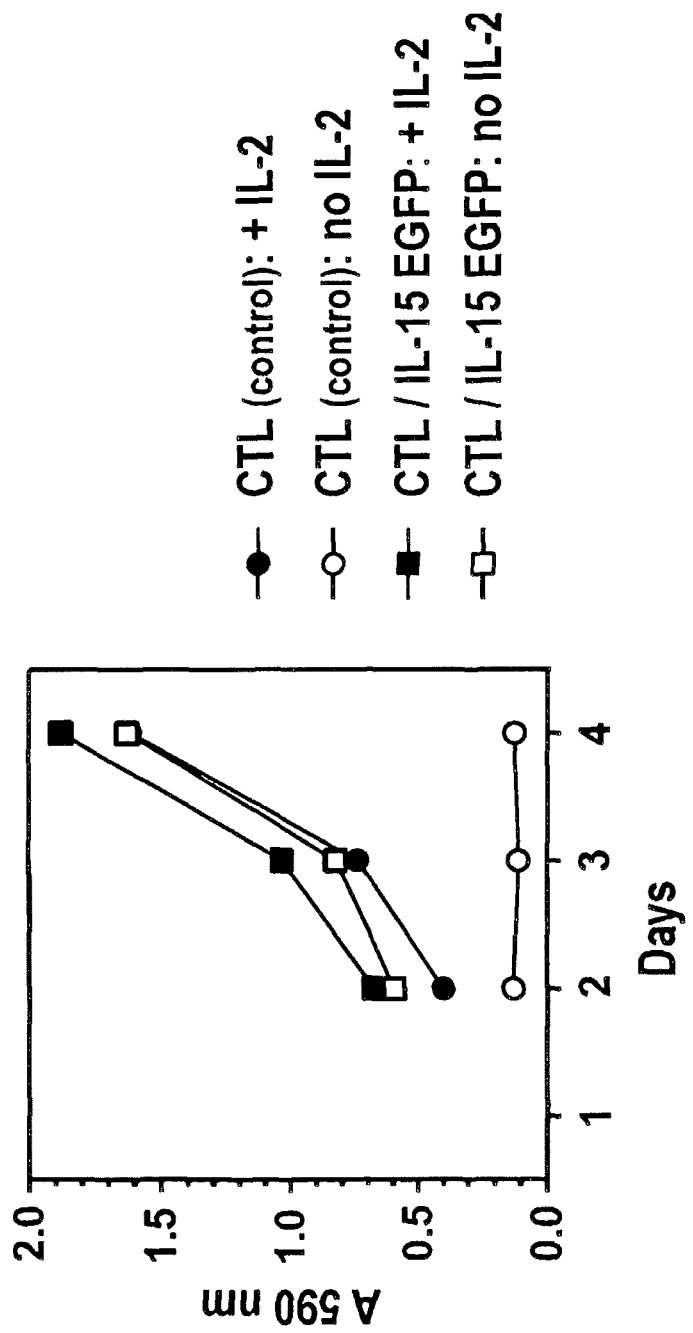

FIG. 5 Growth of IL-15 expressing cytotoxic T lymphocytes in the absence of exogenous cytokines. Cytotoxic T lymphocytes (CTL) were transduced with a lentiviral vector encoding IL-15 as a selectable marker followed by an internal ribosome entry site and enhanced green fluorescent protein (EGFP) as a gene of interest (see FIG. 1B). Transduced CTL (CTL/IL-15 EGFP) or untransduced CTL as controls were either grown in regular growth medium containing 50 IU/mL IL-2 (+IL-2), or in the same medium lacking exogenous cytokines (no IL-2) as indicated. At different time points cell growth was analyzed in MIT cell viability assays. While no significant growth of untransduced CTL was observed in the absence of exogenous cytokines (open circles), CTL expressing IL-15 as a selectable marker continued to grow in the absence of IL-2 (open boxes) and displayed growth kinetics similar to control CTL grown in the presence of IL-2 (filled circles) and CTL expressing IL-15 grown in the presence of IL-2 (filled boxes).

Figure 4:
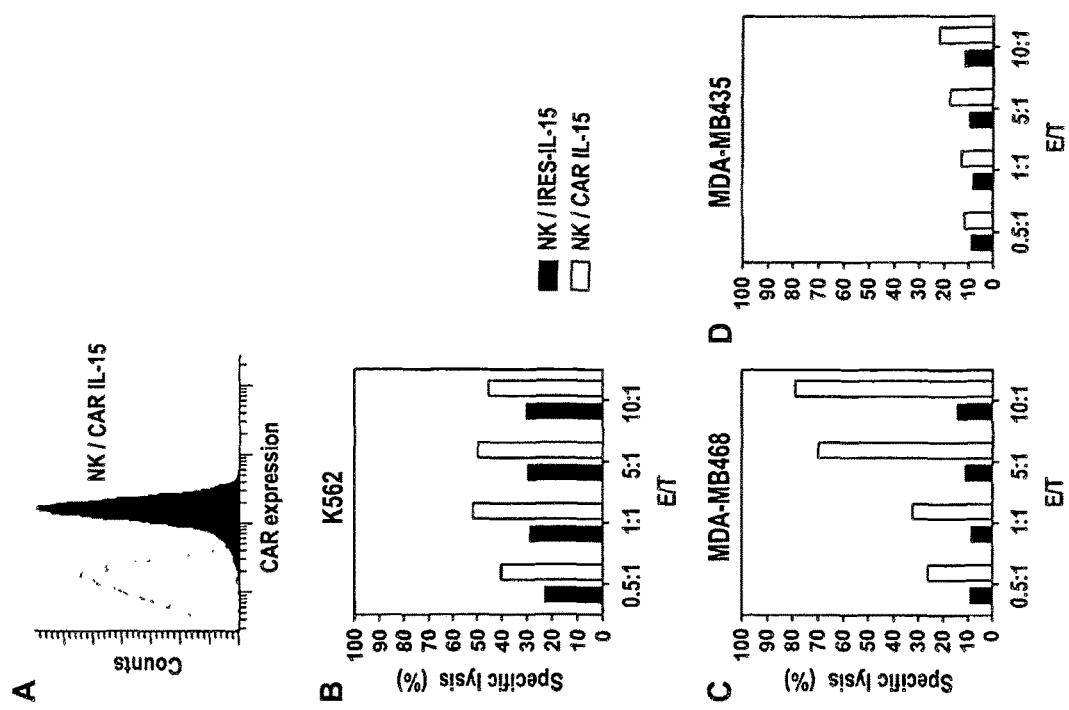
FIG. 4. Cytotoxic activity of NK cells expressing CAR and IL-15. NK cells were transduced with a lentiviral vector encoding an EpCAM-specific chimeric antigen receptor (CAR) followed by an internal ribosome entry site and IL-15 as a selectable marker (NK/CAR IL-15; see FIG. 1C). Control cells were transduced with a lentiviral vector only encoding IL-15 downstream of an IRES sequence (NK/IRES-IL-15; see FIG. 1A). Gene-modified, IL-15 expressing cells were selected by withdrawal of exogenous IL-2 from the culture medium.
Figure 6:
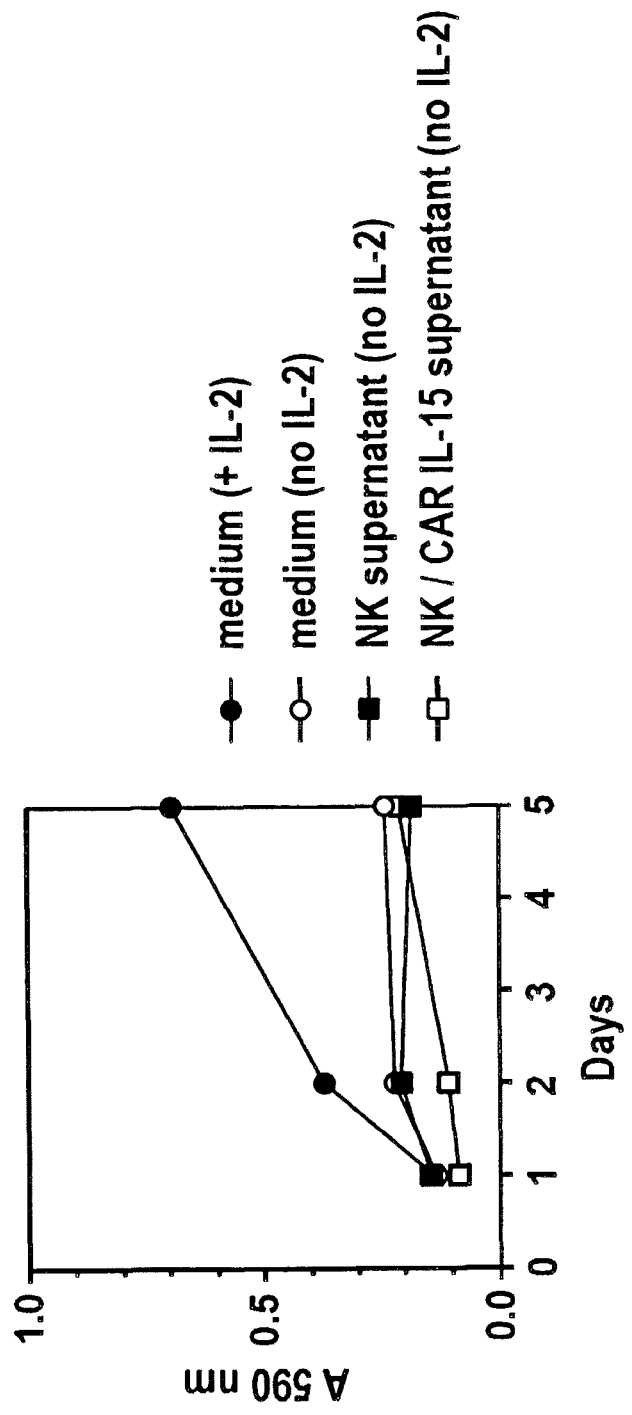

FIG. 6 IL-15 bioactivity in culture supernatant of IL-15 expressing NK cells. NK cells were transduced with a lentiviral vector encoding an EpCAM-specific CAR followed by an internal ribosome entry site and IL-15 as a selectable marker, and gene-modified, IL-15 expressing cells were selected by withdrawal of exogenous IL-2 from the culture medium as described in the legend for FIG. 4. Conditioned culture medium was collected from CAR and IL-15 expressing NK cells grown in the absence of IL-2 (NK/CAR/IL-15), and as a control from untransduced NK cells that were left in medium without IL-2 (NK). Then the growth of IL-2/IL-15-dependent murine CTLL-2 cells in the presence of the conditioned culture medium was analyzed at different time points in MIT cell viability assays in comparison to growth of CTLL-2 cells in regular growth medium containing 50 IU/mL IL-2 (+IL-2) or regular growth medium lacking IL-2 (no IL-2). While CTLL-2 indicator cells continued to grow in regular growth medium containing exogenous IL-2 (filled circles), conditioned medium from CAR and IL-15 expressing NK cells (filled boxes) and untransduced NK cells (open circles), and regular growth medium lacking exogenous IL-2 (open boxes) did not support growth of CTLL-2 cells.

EXAMPLES

Example 1

Figure 1:
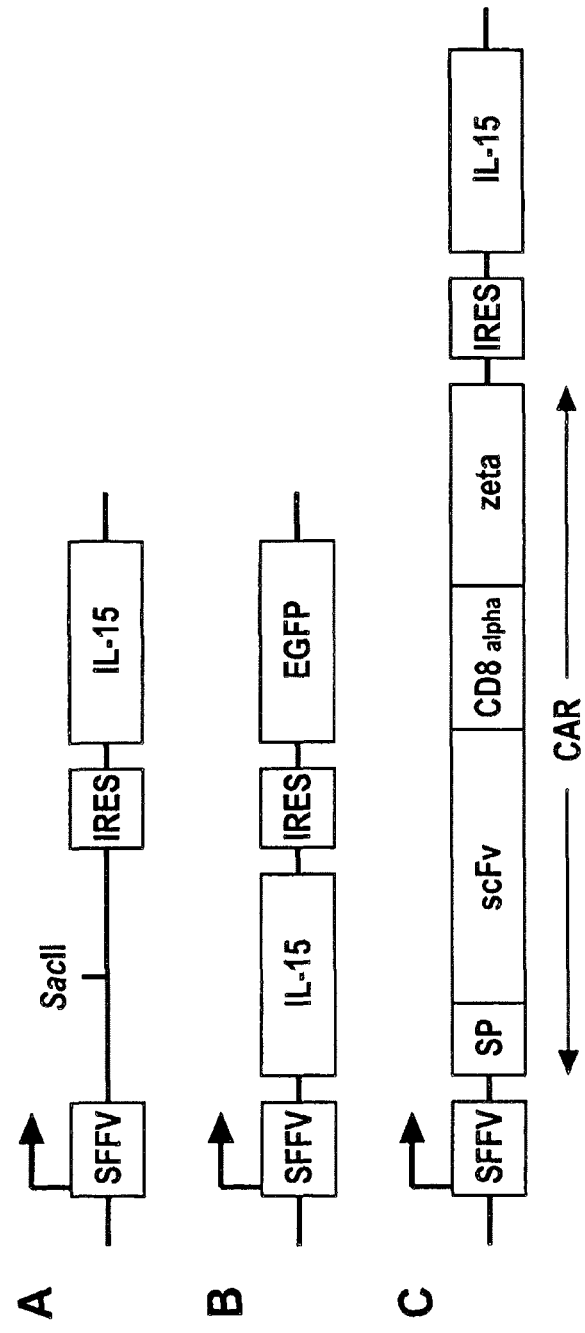
FIG. 1 Schematic representation of expression constructs.
(A) Lentiviral transfer vector with IL-15 cDNA inserted as a selectable marker downstream of an internal ribosome entry site (IRES). The vector also contains a SacII cloning site for the insertion of a gene of interest. Expression is driven by the Spleen Focus Forming Virus promoter (SFFV).
(B) Lentiviral transfer vector encoding IL-15 under the control of the SFFV promoter and followed by an IRES sequence and cDNA encoding enhanced green fluorescent protein (EGFP) as a marker.
(C) Lentiviral transfer vector encoding a chimeric antigen receptor (CAR) as a gene of interest under the control of the SFFV promoter, followed by an IRES sequence site and IL-15 cDNA as a selectable marker. The CAR is composed of immunoglobulin heavy chain signal peptide (SP), a single-chain Fv antibody fragment specific for a target cell surface antigen (scFv), a CD8 alpha-chain hinge region as a flexible linker (CD8 alpha), and CD3 zeta-chain or a composite CD28-CD3 zeta-chain fusion as a signaling domain (zeta).

Generation of IL-15 expression constructs. Different lentiviral vectors based on SIEW were used to analyze the suitability of interleukin-15 (IL-15) as a selectable marker for enrichment of gene-modified lymphocytes. In all vectors, expression of IL-15 and additional genes is driven by a spleen focus forming virus promoter (SFFV). For expression of IL-15 as a single gene of interest, cDNA encoding human IL-15 was inserted downstream of an internal ribosome entry site (IRES) in lentiviral vector SLEW (FIG. 1A). To analyze functionality of IL-15 as a selectable marker and IL-15 mediated selection of cells co-expressing IL-15 and enhanced green fluorescent protein (EGFP) as a model gene of interest, IL-15 cDNA was inserted upstream of an IRES sequence and cDNA encoding EGFP in lentiviral vector SIEW (FIG. 1B). To analyze functionality of IL-15 as a selectable marker and IL-15 mediated selection of cells co-expressing IL-15 and a chimeric antigen receptor (CAR) as a gene of interest with therapeutic activity, a bicistronic vector was generated that encodes a CAR, followed by an IRES sequence and IL-15 cDNA (FIG. 1C). The CAR is composed of an immunoglobulin heavy chain signal peptide, a single-chain Fv antibody fragment specific for a target cell surface antigen on tumor cells, a CD8 alpha-chain hinge region as a flexible linker, and CD3 zeta-chain as a signaling domain.

Transduction of NK cells and CTL. VSV-G pseudotyped lentiviral vector particles were produced by transient triple transfection of 293T cells with the transfer vector together with the packaging constructs pMD-VSVG and 8.91. Lentiviral vector was used for transduction of NK cells and CTL, and successfully transduced NK cells and CTL were selected by IL-2 withdrawal starting two days after transduction.

Figure 2:
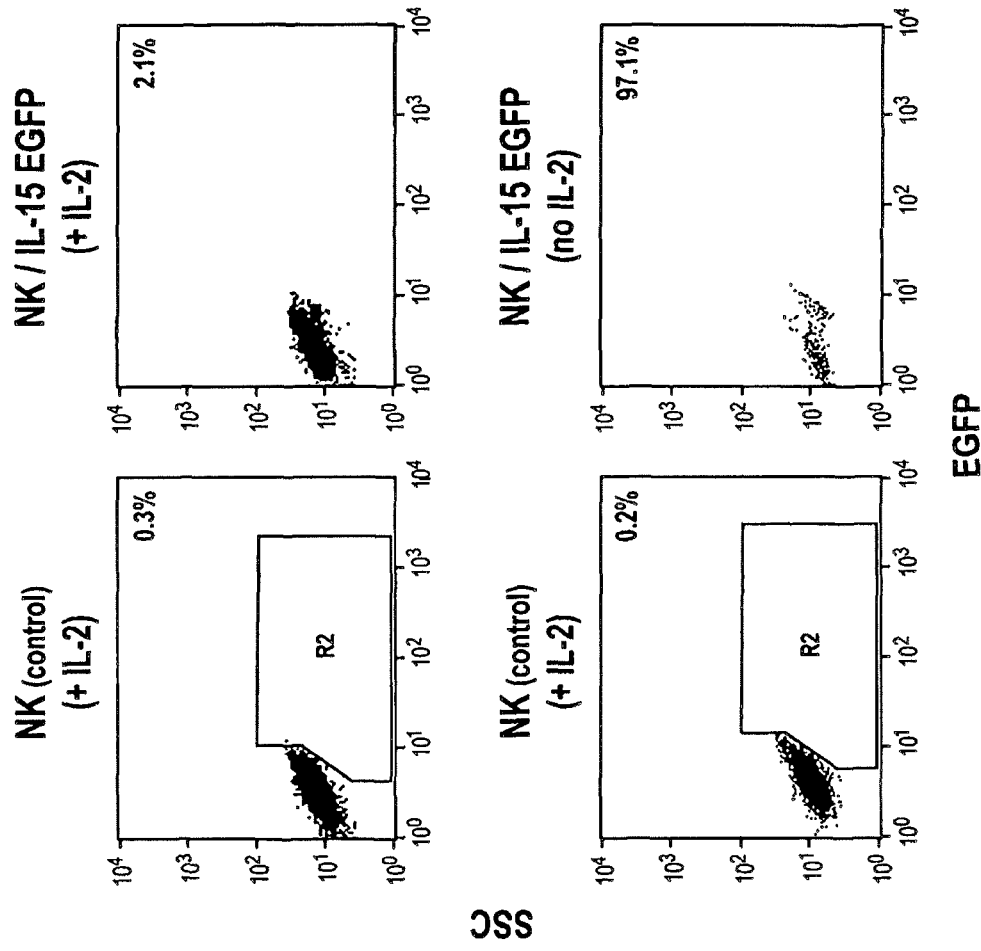
FIG. 2 Selective enrichment of NK cells expressing IL-15 as a selectable marker. NK cells were transduced with a lentiviral vector encoding IL-15 as a selectable marker followed by an internal ribosome entry site and enhanced green fluorescent protein (EGFP) as a gene of interest (NK/IL-15 EGFP; see FIG. 1B). EGFP expression of cells was analyzed by flow cytometry at different time points after transduction. Maintenance of the pool of transduced NK cells in regular growth medium containing 100 IU/mL IL-2 did not result in selective enrichment of EGFP expressing cells (upper right panel) when compared to untransduced NK cells (left panels). Maintenance of the pool of transduced NK cells in growth medium without IL-2 for 14 days resulted in selective enrichment of successfully transduced NK cells co-expressing IL-15 and EGFP (lower right panel).

Selective enrichment of NK cells expressing IL-15 as a selectable marker. The functionality of IL-15 as a selectable marker for enrichment of gene-modified lymphocytes was tested by transduction of NK cells with a lentiviral vector encoding IL-15 followed by an internal ribosome entry site and enhanced green fluorescent protein (EGFP) as a gene of interest. The transduction rate in this experiment was approximately 2% indicated by the proportion of EGFP-positive cells, which remained at this level upon culture in medium containing exogenous IL-2 (FIG. 2). In contrast, culture of transduced cells in selection medium lacking exogenous cytokines for 14 days resulted in selective enrichment of gene-modified cells indicated by a marked increase of EGFP-positive cells to approximately 97% (FIG. 2). These results demonstrate that IL-15 is effective as a selectable marker gene in a bicistronic vector, allowing enrichment of gene-modified lymphocytes expressing IL-15 together with another gene of interest. Furthermore, IL-15 is sufficient to support long-term growth and survival of the selected lymphocytes in the absence of exogenous cytokines.

Figure 3:
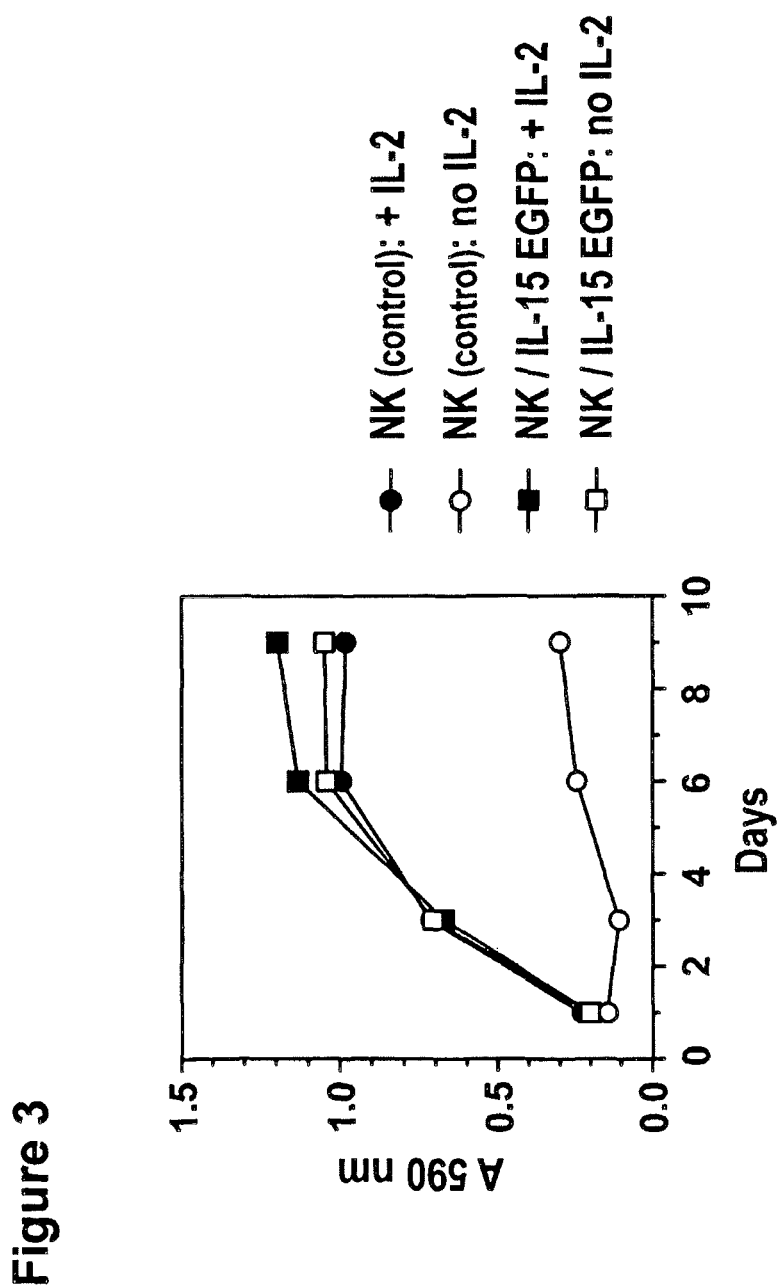
FIG. 3 Growth of IL-15 expressing NK cells in the absence of exogenous cytokines. NK cells were transduced with a lentiviral vector encoding IL-15 as a selectable marker followed by an internal ribosome entry site and enhanced green fluorescent protein (EGFP) as a gene of interest (see FIG. 1B). Transduced NK cells (NK/IL-15 EGFP) or untransduced NK cells as controls were either grown in regular growth medium containing 100 IU/mL IL-2 (+IL-2), or in the same medium lacking exogenous cytokines (no IL-2) as indicated. At different time points cell growth was analyzed in MIT cell viability assays. While no significant growth of untransduced NK cells was observed in the absence of exogenous cytokines (open circles), NK cells expressing IL-15 as a selectable marker continued to grow in the absence of IL-2 (open boxes) and displayed growth kinetics similar to control NK cells grown in the presence of IL-2 (filled circles).

Growth of IL-15 expressing NK cells and CTL in the absence of exogenous cytokines. Proliferation of NK cells and CTL expressing IL-15 as a selectable marker and EGFP as a gene of interest was analyzed in MIT cell viability assays. Untransduced NK cells and CTL served as control. While no significant growth of untransduced NK cells and CTL was observed in the absence of exogenous cytokines, NK cells (FIG. 3) and CTL (FIG. 5) expressing IL-15 as a selectable marker continued to grow in the absence of IL-2 and displayed growth kinetics similar to control NK cells and CTL grown in the presence of IL-2. These results demonstrate that expression of IL-15 as a selectable marker is sufficient to support long-term growth and survival of cytotoxic lymphocytes in the absence of exogenous cytokines.

Expression of chimeric antigen receptor and cytotoxic activity of NK cells selected using IL-15 as a selectable marker. Expression and functionality of chimeric antigen receptors in NK cells transduced with a lentiviral vector encoding a CAR as a gene of interest and IL-15 as a selectable marker was tested by flow cytometry and in FACS-based cytotoxicity assays. NK cells were transduced with a lentiviral vector encoding an EpCAM-specific chimeric antigen receptor (CAR) followed by an internal ribosome entry site and IL-15 as a selectable marker. Gene-modified, IL-15 expressing cells were selected by withdrawal of exogenous IL-2 from the culture medium. Expression of CAR on the surface of selected cells was investigated by FACS analysis using an antibody detecting a sequence tag included in the EpCAM-specific CAR. It was found that selection for IL-15 expressing cells by IL-2 withdrawal resulted in a surviving cell population homogeneously expressing CAR on the cell surface (FIG. 4A). Functionality of these cells was tested in cytotoxicity assays without addition of exogenous cytokines. Thereby NK cells co-expressing EpCAM-specific CAR and IL-15, and NK cells only expressing IL-15 displayed similar cytotoxic activity towards NK-sensitive K562 erythroleukemic control cells, but only little activity against NK-resistant and EpCAM-negative MDA-MB435 melanoma cells (FIG. 4B, D), When cytotoxic activity towards EpCAM-positive MDA-MB468 breast carcinoma cells was tested, NK cells co-expressing the EpCAM-specific CAR and IL-15 showed EpCAM-specific and highly effective cell killing, while control cells only expressing IL-15 did not (FIG. 4C). These results demonstrate that IL-15 is effective as a selectable marker gene in a bicistronic vector, allowing enrichment of cytotoxic lymphocytes expressing a CAR as a gene of interest. Furthermore, IL-15 facilitates full functionality of the selected lymphocytes in the absence of exogenous cytokines.

IL-15 bioactivity in culture supernatant of IL-15 expressing NK cells. To test whether IL -15 is secreted by IL-15 expressing NK cells in amounts sufficient to support survival and growth of non-transduced bystander cells, IL-15 bioactivity in conditioned culture supernatant of IL-15 expressing NK cells was investigated. NK cells were transduced with a lentiviral vector encoding an EpCAM-specific CAR followed by an internal ribosome entry site and IL-15 as a selectable marker as described above. Gene-modified, IL-15 expressing cells were selected by withdrawal of exogenous IL-2 from the culture medium. Conditioned medium from the gene-modified NK cells growing in the absence of IL-2 was collected after three days of culture, and the ability of untransduced IL-2/IL-15-dependent CTLL-2 cells to grow in the presence of conditioned NK cell medium was analyzed in MTT cell viability assays. Conditioned medium from untransduced NK cells served as control. While significant growth of CTLL-2 cells was observed in regular growth medium containing IL-2, conditioned medium from CAR and IL-15 expressing NK cells like conditioned medium from untransduced NK cells and growth medium lacking IL-2 did not support growth of CTLL-2 cells (FIG. 6). These results demonstrate that IL-15 expressing cytotoxic lymphocytes, while supporting their own growth via ectopic production of IL-15 (see FIGS. 2, 3, 5), do not secrete IL-15 in amounts high enough to also support growth and survival of untransduced bystander cells. Hence, these results further confirm that IL-15 functions as a selectable marker gene in cytotoxic lymphocytes genetically modified with an IL-15 expression construct.

Materials and Methods (of Example 1)

Cells and culture conditions. Human NK cells were maintained in X-VIVO10 medium supplemented with 5% human plasma and 100 IU/mL IL-2. IL-15 expressing NK cells were cultured in X-VIVO10 medium supplemented with 5% human plasma in the absence of exogenous cytokines. Murine CTL were maintained in RPMI 1640 medium supplemented with 10% fetal bovine serum, 2 mM L-glutamine, 100 U/mL penicillin, 100 µg/ml streptomycin, 50 µM β-mercaptoethanol and 50 IU/mL IL-2. IL-15 expressing CTL were cultured in the same medium in the absence of exogenous cytokines.

Construction of IL-15 expression vector. The lentiviral transfer vector SIEW was used as basis for the construction of different IL-15 encoding vectors for expression in lymphocytes.

Two types of bicistronic lentiviral transfer vectors were constructed that employ IL-15 as a selectable marker. First, IL-15 cDNA was inserted into the SacII restriction site of SIEW resulting in a vector encoding IL-15 under the control of the Spleen Focus Forming Virus promoter followed by an internal ribosome entry site (IRES) sequence and enhanced green fluorescent protein (EGFP) cDNA. For a second type of bicistronic vector, the IRES sequence was amplified by PCR using SIEW plasmid DNA as template and the oligonucleotide primers:

```
5'-SacII-IRES
                                        [SEQ ID NO. 5]
5'-AAACCGCGGAAAAAAACTGGCAAGAACTGACGAGTTCGTATTCCCGG

CCGCAGCC-3'
and

3'-XbaI-IRES
                                        [SEQ ID NO. 6]
5'-AAATCTA-GAAAACCACGTCCCCGTGGTTCGGGGGGCCTAG-3'.
```

The resulting PCR product was digested with SacII and XbaI and subcloned into pBluescript SK(−) (pBSK) to generate the plasmid pBSK-IRES. IL-15 cDNA was amplified using the oligonucleotide primers:

```
5'-XbaI-IRES-IL15
                                        [SEQ ID NO. 7]
5'-AAATCTAGAATGAGAATTTCGAAACCACATTTGAG-3'
and 3'-SwaI-IRES-IL15
                                        [SEQ ID NO. 8]
5'AAAAAATTTAAATATTATCAAGAAGTGTTGATGAACATTTGG-3'.
```

The resulting PCR product was digested with XbaI and SwaI and ligated into XbaI and EcoRV digested pBSK-IRES to generate pBSK-IRES-IL-15. Then the IRES-IL-15 expression cassette was isolated by digestion with SacII and HincII, and ligated into SacII and SwaI digested lentiviral transfer vector SIEW. The resulting vector contains a SacII restriction site for insertion of a gene of interest, followed by an IRES sequence and IL-15 cDNA as a selectable marker. Chimeric antigen receptor sequences were inserted via SacII resulting in vectors encoding a CAR as a gene of interest, followed by an IRES sequence and IL-15 cDNA for selection.

Production of VSV-G pseudotyped vectors in 293T cells. Vector particles were generated by transient transfection of $4 \times 10^6$ HEK-293T cells with a three plasmid system consisting of the packaging plasmid coding for the VSV-G envelope protein (pMD-VSVG), the glycoprotein expression plasmid encoding gag and poi (8.91), and the transfer plasmid carrying the gene of interest. Cells were transfected by calcium phosphate transfection using a total of 20 μg plasmid DNA consisting of 6.5 μg gag pol, 3.5 μg VSV-G, and 10 μg of transfer plasmids. DNA-calcium phosphate-precipitates were added dropwise to cell monolayers, and 10 mM chloroquine were added. Cell culture supernatants containing pseudotyped lentiviral vector particles were harvested 48 h later. Supernatants were sterile filtered (0.45 μm filter) and directly used for transduction of NK cells and CTL.

Lentiviral transduction. For transduction, $5 \times 10^5$ NK cells or CTL were seeded into a single well of a 6 well plate. Vector particles were added to the cells in the presence of 8 μg/mL polybrene and centrifuged for 60 min at 1800 rpm at 32° C. 48 h after transduction the cells were analyzed by FACS for EGFP and CAR expression.

Flow cytometric analysis. For analysis of EGFP expression, transduced NK cells were harvested, washed once in FACS buffer (DPBS, 3% FCS), resuspended in 250 μL, FACS buffer, and directly analyzed using a FACSCanto flow cytometer (BD Biosciences). Untransduced cells served as control. For analysis of CAR expression, washed NK cells were incubated with 1 μg CAR-specific antibody (EpCAM-specific CAR) or 1 μg ErbB2-Fc fusion protein (R&D Systems) (ErbB2-specific CAR) for 1 h at 4° C. Then cells were washed and stained with a species-specific secondary APC-coupled antibody for 20 min at 4° C. Samples were washed in FACS buffer and resuspended in 250 μl for FACS analysis using a FACSCanto flow cytometer (BD Biosciences). NK cells transduced with an IL-15 expression construct served as control.

Cell growth kinetics. NK cells or CTL were seeded in triplicates in 96-well plates at a density of $1 \times 10^4$ cells/well in normal growth medium with or without addition of 100 IU/mL IL-2 (NK cells) or 50 IU/mL IL-2 (CTL). The cells were incubated for up to 9 days at 37° C. in a humidified atmosphere of 95% air, 5% $CO_2$. At different time points (days 1, 3, 6, 9 for NK cells; days 2, 3, 4 for CTL) the relative number of viable cells was determined in MTT metabolization assays. Ten μL of 10 mg/mL MTT [3-(4,5-dimethylthiazol-2-yl)-2,5-diphenyl-2H-tetrazolium bromide] (Sigma, Deisenhofen, Germany) in DPBS were added to each well, and the cells were incubated for 4 hours. Cells were then lysed by the addition of 90 μL 20% SDS in 50% dimethyl formamide, pH 4.7. After solubilisation, color development due to formation of a brown formazan product was quantified by determining the absorbance at 590 nm in a microplate reader. Samples without cells served as blank.

FACS-based cytotoxicity assays. To investigate cytotoxic activity of parental and genetically modified NK cells (effector cells, E) towards different tumor cell lines (target cells, T), a FACS-based cytotoxicity assay was used. Target cells were labeled with calcein violet AM (Molecular Probes, Invitrogen). Cells were harvested, counted and washed in calcein wash buffer (RPMI1640). The cell number was adjusted to $4 \times 10^6$ cells/mL, and 1.5 μL calcein violet AM dissolved in 42 μL DMSO were added to the cells. Staining of cells was performed for 30 min on ice. Then cells were washed three times with calcein wash buffer, and the cell number was adjusted to $5 \times 10^5$ cells/mL. To test cytotoxic activity of genetically modified NK cells, effector and labeled target cells were co-cultured at various effector to target (E/T) ratios. First, effector cells were pelleted, counted and the cell number was adjusted to $5 \times 10^6$ cells/mL. Appropriate dilutions were prepared. For co-culture experiments target cells were resuspended in X-VIVO medium containing 5% human plasma without addition of exogenous cytokines. 100 μL target cells were co-cultured with 100 μL effector cells at various E/T ratios for 2 h at 37° C. Then samples were washed once in FACS buffer. Spontaneous target-cell lysis was determined in samples only containing labeled target cells. 250 μL propidium iodide solution (1 μg/mL) were added to the samples shortly before measurement. Cells were analyzed in a FACSCanto flow cytometer (BD Biosciences). The percentage of dead target cells was determined using FACSDiVa software (BD Biosciences).

IL-15 activity in culture supernatant of IL-15 expressing cytotoxic lymphocytes. For analysis of soluble IL-15 activity in the supernatant of NK cells transduced with a lentiviral vector encoding an EpCAM-specific CAR followed by an internal ribosome entry site and IL-15 as a selectable marker, conditioned medium from $1 \times 10^6$ gene-modified NK cells grown for three days in 10 mL of growth medium without IL-2 was collected and sterile filtered. Subsequently, IL-2/IL-15-dependent murine CTLL-2 cells (ATCC number TIB- 214) were seeded in triplicates in 96-well plates at a density of 1×10⁴ cells/well in conditioned culture supernantant of gene-modified NK cells. CTLL-2 cells grown in culture supernatant of untransduced NK cells left in medium lacking IL-2, and CTLL-2 cells grown in regular growth medium with or without the addition of 50 IU/mL IL-2 served as controls. The cells were incubated for up to 5 days at 37° C. in a humidified atmosphere of 95% air, 5% $CO_2$. At different time points (days 1, 2, 5) the relative number of viable cells was determined in MTT metabolization assays as described above for the determination of cell growth kinetics.

REFERENCES

Uherek C, Groner B, Wels W. Chimeric antigen receptors for the retargeting of cytotoxic effector cells. *J. Hematother. Stem Cell Res.* 10: 523-543, 2001.

Uherek C, Tonn T, Uherek B, Becker S, Schnierle B, Klingemann H G, Wels W. Retargeting of natural killer-cell cytolytic activity to ErbB2 expressing cancer cells results in efficient and selective tumor cell destruction. *Blood* 100: 1265-1273, 2002.

Müller T, Uherek C, Maki G, Chow K U, Schimpf A, Klingemann H G, Tonn T, Wels W S. Expression of a CD20-specific chimeric antigen receptor enhances cytotoxic activity of NK cells and overcomes NK-resistance of lymphoma and leukemia cells. *Cancer Immunol. Immunother.* 57: 411-423, 2008.

Tavri S, Jha P, Meier R, Henning TD, Müllner T, Hostetter D, Knopp C, Johannson M, Reinhart V, Boddington S, Sista A, Wels W S, Daldrup-Link H E. Optical imaging of cellular immunotherapy against prostate cancer. *Mol. Imaging* 8: 15-26, 2009.

Zhang J, Sun R, Wei H, Zhang J, Tian Z. Characterization of interleukin-15 gene-modified human natural killer cells: implications for adoptive cellular immunotherapy. *Haematologica.* 89:338-347, 2004.

Wuest T Y, Willette-Brown J, Durum S K, Hurwitz A A. The influence of IL-2 family cytokines on activation and function of naturally occurring regulatory T cells. *J. Leukoc. Biol.* 84:973-98, 2008.

The invention claimed is:

1. A method for ex vivo or in vitro gene transfer into an isolated mammalian cell,
   wherein said method comprises the use of interleukin-15 (IL-15) as a selectable marker,
   wherein the isolated mammalian cell is a T lymphocyte (T cell) or natural killer (NK) cell,
   wherein the method comprises the transfer, into the isolated mammalian cell, of one or more expression constructs comprising a first nucleotide sequence encoding IL-15 and a second nucleotide sequence encoding a protein of interest, which is a protein other than IL-15, and
   wherein the protein of interest is a protein of therapeutic interest, said one or more expression constructs encoding IL-15 being selected from a lentiviral vector, a gamma-retroviral vector, and an adeno-associated virus vector,
   wherein the expression of the IL-15 as a selectable marker results in survival or growth of the isolated mammalian T cell or NK cell in the absence of exogenously added cytokines, and
   wherein the IL-15 has the amino acid sequence of SEQ ID NO. 1 or an amino acid sequence that has at least 95% sequence identity to SEQ ID NO. 1, or the IL-15 is encoded by the nucleotide sequence of SEQ ID NO. 2 or a nucleotide sequence with at least 95% sequence identity to SEQ ID NO. 2, and
   wherein the expression of the IL-15 does not result in the secretion of IL-15 into the culture supernatant in amounts sufficient to support survival and growth of cells that are not transformed or transduced with the IL-15 and/or are not expressing the IL-15 themselves.

2. The method according to claim 1, wherein the expression of the IL-15 as a selectable marker results in survival or growth of the isolated mammalian T cell or NK cell in the absence of exogenously added IL-2.

3. The method according to claim 1, wherein the IL-15 is encoded by:
   a nucleotide sequence encoding human IL-15 having the amino acid sequence of SEQ ID NO. 1,
   a nucleotide sequence comprising the nucleotide sequence of human IL-15 transcript variant 3 of SEQ ID NO. 2,
   or a complementary sequence of the nucleotide sequence encoding the full length human IL-15 of SEQ ID NO. 1 or SEQ ID NO. 2,
   or a codon-optimized sequence of the nucleotide sequence encoding the full length human IL-15 of SEQ ID NO. 1 or SEQ ID NO. 2,
   or a nucleotide sequence encoding an amino acid sequence with at least 95% sequence identity to the amino acid sequence of SEQ ID NO. 1,
   or a nucleotide sequence with at least 95% sequence identity to the nucleotide sequence of SEQ ID NO. 2.

4. The method according to claim 1, wherein the protein of therapeutic interest is a chimeric antigen receptor (CAR) that comprises the following:
(i) a signal peptide;
(ii) a target specific recognition domain that binds an antigen, receptor, peptide ligand or protein ligand of the target, wherein the target is a cell or a virus;
(iii) a linker region, connecting domain (ii) and domain (iv); and
(iv) an effector domain comprising a transmembrane region and one or more intracellular signaling domains.

5. The method according to claim 4, wherein the target specific recognition domain (ii) of the CAR comprises
an antigen binding domain derived from an antibody against an antigen of the target, or
a peptide that binds an antigen of the target, or
a peptide or protein that binds an antibody that binds an antigen of the target, or
a peptide or protein ligand that binds a receptor on the target, or
a domain derived from a receptor that binds a peptide or protein ligand on the target,
and/or, where domain (ii) of the CAR binds an antigen of the target, wherein the antigen is a tumor-associated surface antigen, a lineage-specific or tissue-specific surface antigen or a virus-specific surface antigen;
and/or, where domain (ii) of the CAR comprises an antigen binding domain, which is derived from an antibody or a single chain variable fragment (scFv).

6. The method according to claim 4, wherein the linker region (iii) of the CAR comprises a hinge region derived from the human CD8 alpha-chain and/or wherein the effector domain (iv) of the CAR comprises the zeta-chain of the human CD3 complex of the T-cell receptor.

7. The method according to claim 1, wherein the T lymphocyte (T cell) is a cytotoxic T lymphocyte (CTL).

* * * * *

```
                       SEQUENCE LISTING

<160> NUMBER OF SEQ ID NOS: 8

<210> SEQ ID NO 1
<211> LENGTH: 162
<212> TYPE: PRT
<213> ORGANISM: Homo sapiens

<400> SEQUENCE: 1

Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
                20                  25                  30

Val Phe Ile Leu Gly Cys Phe Ser Ala Gly Leu Pro Lys Thr Glu Ala
            35                  40                  45

Asn Trp Val Asn Val Ile Ser Asp Leu Lys Lys Ile Glu Asp Leu Ile
    50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
    130                 135                 140

Lys Glu Phe Leu Gln Ser Phe Val His Ile Val Gln Met Phe Ile Asn
145                 150                 155                 160

Thr Ser

<210> SEQ ID NO 2
<211> LENGTH: 489
<212> TYPE: DNA
<213> ORGANISM: Homo sapiens

<400> SEQUENCE: 2
atgagaattt cgaaaccaca tttgagaagt atttccatcc agtgctactt gtgtttactt      60
```

| | | | | |
|---|---|---|---|---|
| ctaaacagtc | attttctaac | tgaagctggc | attcatgtct | tcattttggg | ctgtttcagt | 120 |
| gcagggcttc | ctaaaacaga | agccaactgg | gtgaatgtaa | taagtgattt | gaaaaaaatt | 180 |
| gaagatctta | ttcaatctat | gcatattgat | gctactttat | atacggaaag | tgatgttcac | 240 |
| cccagttgca | aagtaacagc | aatgaagtgc | tttctcttgg | agttacaagt | tatttcactt | 300 |
| gagtccggag | atgcaagtat | tcatgataca | gtagaaaatc | tgatcatcct | agcaaacaac | 360 |
| agtttgtctt | ctaatgggaa | tgtaacagaa | tctggatgca | aagaatgtga | ggaactggag | 420 |
| gaaaaaaata | ttaaagaatt | tttgcagagt | tttgtacata | ttgtccaaat | gttcatcaac | 480 |
| acttcttga | | | | | 489 |

<210> SEQ ID NO 3
<211> LENGTH: 62
<212> TYPE: PRT
<213> ORGANISM: Homo sapiens

<400> SEQUENCE: 3

Ala Leu Ser Asn Ser Ile Met Tyr Phe Ser His Phe Val Pro Val Phe
1               5                   10                  15

Leu Pro Ala Lys Pro Thr Thr Thr Pro Ala Pro Arg Pro Pro Thr Pro
            20                  25                  30

Ala Pro Thr Ile Ala Ser Gln Pro Leu Ser Leu Arg Pro Glu Ala Cys
        35                  40                  45

Arg Pro Ala Ala Gly Gly Ala Val His Thr Arg Gly Leu Asp
    50                  55                  60

<210> SEQ ID NO 4
<211> LENGTH: 163
<212> TYPE: PRT
<213> ORGANISM: Homo sapiens

<400> SEQUENCE: 4

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Arg Arg Lys Asn Pro Gln Glu Gly Leu Tyr Asn Glu
            100                 105                 110

Leu Gln Lys Asp Lys Met Ala Glu Ala Tyr Ser Glu Ile Gly Met Lys
        115                 120                 125

Gly Glu Arg Arg Arg Gly Lys Gly His Asp Gly Leu Tyr Gln Gly Leu
    130                 135                 140

Ser Thr Ala Thr Lys Asp Thr Tyr Asp Ala Leu His Met Gln Ala Leu
145                 150                 155                 160

Pro Pro Arg

<210> SEQ ID NO 5
<211> LENGTH: 55

```
<212> TYPE: DNA
<213> ORGANISM: Artificial
<220> FEATURE:
<223> OTHER INFORMATION: primer

<400> SEQUENCE: 5
aaaccgcgga aaaaaactgg caagaactga cgagttcgta ttcccggccg cagcc          55

<210> SEQ ID NO 6
<211> LENGTH: 40
<212> TYPE: DNA
<213> ORGANISM: Artificial
<220> FEATURE:
<223> OTHER INFORMATION: primer

<400> SEQUENCE: 6
aaatctagaa aaccacgtcc ccgtggttcg gggggcctag                           40

<210> SEQ ID NO 7
<211> LENGTH: 35
<212> TYPE: DNA
<213> ORGANISM: Artificial
<220> FEATURE:
<223> OTHER INFORMATION: primer

<400> SEQUENCE: 7
aaatctagaa tgagaatttc gaaaccacat ttgag                                35

<210> SEQ ID NO 8
<211> LENGTH: 42
<212> TYPE: DNA
<213> ORGANISM: Artificial
<220> FEATURE:
<223> OTHER INFORMATION: primer

<400> SEQUENCE: 8
aaaaaattta aatattatca agaagtgttg atgaacattt gg                        42
```